US012694526B2

(12) United States Patent
Namías et al.

(10) Patent No.: US 12,694,526 B2
(45) Date of Patent: Jul. 28, 2026

(54) METHOD FOR QUANTIFYING MYOCARDIAL BLOOD FLOW FROM A NUCLEAR MEDICINE TOMOGRAPHIC IMAGE

(71) Applicants: FUNDACIÓN CENTRO DIAGNÓSTICO NUCLEAR, Buenos Aires (AR); COMISIÓN NACIONAL DE ENERGÍA ATÓMICA, Buenos Aires (AR); UNIVERSIDADE DE COIMBRA, Coimbra (PT)

(72) Inventors: Mauro Namías, Buenos Aires (AR); Aley Palau San Pedro, Buenos Aires (AR); Antero José Pena Afonso De Abrunhosa, Coimbra (PT)

(73) Assignees: FUNDACIÓN CENTRO DIAGNÓSTICO NUCLEAR, Buenos Aires (AR); COMISIÓN NACIONAL DE ENERGÍA ATÓMICA, Buenos Aires (AR); UNIVERSIDADE DE COIMBRA, Argentina Coimbra (PT)

( * ) Notice: Subject to any disclaimer, the term of this patent is extended or adjusted under 35 U.S.C. 154(b) by 245 days.

(21) Appl. No.: 18/719,089

(22) PCT Filed: Dec. 14, 2022

(86) PCT No.: PCT/PT2022/050033
§ 371 (c)(1),
(2) Date: Jun. 12, 2024

(87) PCT Pub. No.: WO2023/113630
PCT Pub. Date: Jun. 22, 2023

(65) Prior Publication Data
US 2024/0420324 A1 Dec. 19, 2024

(30) Foreign Application Priority Data
Dec. 15, 2021 (AR) .............................. 20210103514

(51) Int. Cl.
*G06T 7/00* (2017.01)
*A61B 5/00* (2006.01)
*A61B 5/026* (2006.01)

(52) U.S. Cl.
CPC .......... *G06T 7/0012* (2013.01); *A61B 5/0044* (2013.01); *A61B 5/026* (2013.01);
(Continued)

(58) Field of Classification Search
CPC ......... G06T 7/0012; G06T 2207/10104; G06T 2207/10108; A61B 5/0044; A61B 5/026
See application file for complete search history.

(56) References Cited

U.S. PATENT DOCUMENTS 6,504,157 B2 1/2003 Juhi
7,683,331 B2 3/2010 Chang
(Continued)

FOREIGN PATENT DOCUMENTS

CN 100374877 C 3/2008
CN 111436959 A 7/2020
(Continued)

OTHER PUBLICATIONS

Klein et al., "Quantification of myocardial blood flow and flow reserve: Technical aspects", Journal of Nuclear Cardiology, 2010, vol. 17, No. 4, pp. 555-570.
(Continued)

*Primary Examiner* — Delomia L Gilliard
(74) *Attorney, Agent, or Firm* — LUCAS & MERCANTI, LLP

(57) ABSTRACT
A method for quantifying myocardial blood flow (F) from a single static tomographic image of nuclear medicine, having a stage of processing the tomographic image, and a stage of calculating the myocardial blood flow, wherein the integral of the activity versus time concentration curve of the blood
(Continued)

concentration of the radiotracer is calculated from a single time sampling point.

10 Claims, 5 Drawing Sheets

(52) U.S. Cl.
    CPC .............. *G06T 2207/10104* (2013.01); *G06T 2207/10108* (2013.01)

(56) References Cited

U.S. PATENT DOCUMENTS

| | | | |
|---|---|---|---|
| 7,705,316 B2 | 4/2010 | Rousso et al. | |
| 7,968,851 B2 | 6/2011 | Rousso et al. | |
| 10,258,247 B2 * | 4/2019 | Nishida ................ | A61B 5/7203 |
| 2019/0290232 A1 * | 9/2019 | Garg ..................... | A61B 6/037 |

FOREIGN PATENT DOCUMENTS

| | | | | |
|---|---|---|---|---|
| JP | 4895080 B2 | 3/2012 | | |
| WO | WO-2005044104 A1 * | 5/2005 | ........... | G01R 33/563 |

OTHER PUBLICATIONS

Bailing "PET tracers and techniques for measuring myocardial blood flow in patients with coronary artery disease", Journal of Biomedical Research, 2013, vol. 27, No. 6, pp. 452-459.

Van Den Hoff et al., "Correction of scan time dependence of standard uptake values in oncological PET Background", EJNMMI Research, 2014, vol. 4, No. 18, pp. 1-14.

International Search Report and Written Opinion for Corresponding International Application No. 14 pages, Mar. 3, 2023.

* cited by examiner $$\frac{dC_1}{dx} = K1Ca(t) - (K2 + K3)C_1(t) + K4C_2(t)$$

METHOD FOR QUANTIFYING MYOCARDIAL BLOOD FLOW FROM A NUCLEAR MEDICINE TOMOGRAPHIC IMAGE

CROSS-REFERENCE TO RELATED APPLICATIONS

This application is a 371 of PCT/PT2022/050033, filed Dec. 14, 2022, which claimed the priority of Argentina application No. 20210103514, filed Dec. 15, 2021, the contents of each of which are incorporated herein by reference.

The present invention relates to a method for quantifying myocardial blood flow (F) from a nuclear medicine tomographic image, such as positron emission tomography (PET), single photon emission computed tomography (SPECT), and any other nuclear imaging modality that allows reconstructing images of the activity concentration of a radiotracer.

The present invention makes it possible to quantify F from a static tomographic image of nuclear medicine.

TECHNICAL FIELD OF THE INVENTION

The technical field to which the present invention belongs is that of the quantification of physiological parameters of animals, in particular, humans, based on diagnostic images of nuclear medicine.

STATE OF THE ART AND PROBLEMS TO BE SOLVED

The state of the art for the quantification of myocardial blood flow (F) employs compartmental modeling for the estimation of this kinetic parameter (milliliters of blood per gram of tissue per minute). Compartmental models consist of sets of coupled differential equations, wherein each compartment represents a chemical state or spatial location of the tracer (e.g., extracellular space, intracellular space, free tracer, metabolized tracer, etc.). For each particular study, the transfer constants between compartments (kinetic parameters: K1, K2, K3, K4, etc.) that minimize the error between model prediction and measured data are estimated. An example of a two-compartment model is shown in FIG. 1.

These models require knowledge of the input and output functions of the model (activity concentration versus time curves). The input curve generally represents the arterial blood concentration (Ca), and the output curve the concentration in a region of interest where it is desired to estimate blood flow, and they are obtained from dynamic imaging.

In nuclear medicine, dynamic PET or SPECT tomographic imaging (temporal sequence of 3D imaging) is used to quantify over time the Ca(t) and concentration in the myocardium (Cm(t)) from measurements of activity concentration in left ventricular and myocardium imaging (i.e., regions of interests), respectively, in myocardial perfusion studies. An example of activity-time concentration curves is shown in FIG. 2.

The complete solution of the compartmental model can be simplified by considering a single-compartment model with K2=0 [Yoshida K, Mullani N and Gould K L 1996 Coronary flow and flow reserve by PET simplified for clinical applications using rubidium-82 or nitrogen-13-ammonia J. Nucl. Med. 37 1701-12]. In this case, the following equation is proposed:

$$F = \frac{\frac{1}{t_2 - t_1} \int_{t1}^{t2} Cm(t)dt}{E \int_0^{t2} Ca(t)dt} \qquad \text{Equation 1}$$

Where E is the extraction fraction of the radiotracer in the myocardium, F is the myocardial blood flow, Cm(t) is the uptake of the radiotracer in the myocardium at time t after administration of the radiotracer, and Ca(t) is the activity concentration of the radiotracer in the blood (i.e., arterial activity concentration) as a function of time. The extraction fraction E depends on the tissue permeability (PS) for the employed radiotracer and is a function of blood flow. E can be modeled using the Renkin-Crone model, according to the following equation:

$$E = 1 - e^{-\frac{PS}{F}} \qquad \text{Equation 2}$$

Myocardial blood flow can be obtained from K1 considering the extraction fraction E according to the following equation [Bailing Hsu. PET tracers and techniques for myocardial blood flow measurement in patients with coronary artery disease. The Journal of Biomedical Research, 2013, 27(6): 452-459. doi:10.7555/JBR.27.20130136]:

$$K1 = E \cdot F = \frac{Cm(t)}{\int_0^t Ca(t)dt} \qquad \text{Equation 3}$$

This simplified model demonstrated excellent correlation with more complex compartmental models. According to [Chang C. Y., Hung G. U., Hsu B., Yang B. H., Chang C. W., Hu L. H., Huang W. S., Wang H. E., Wu T. C. and Liu R. S. 2020. Simplified quantification of 13N-ammonia PET myocardial blood flow: A comparative study with the standard compartment model to facilitate clinical use. J. Nucl. Cardiol. 27. 819-28: doi.org/10.1007/s12350-018-1450-1], it can be further simplified. In this article, they used a static image between t=0 and t=2 min to estimate the integral of Ca(t) and another static image between t=2 min and t=5 min to estimate Cm(t), using the implementation available in the commercial software HeartSee®. This simplification also demonstrated a good correlation with the flow values estimated by more complex compartmental models.

In practice, although there are already SPECT systems with detectors distributed over an arc of 180 degrees (or more) that allow the acquisition of dynamic tomographic images of the heart with simultaneity at all angles [Patents: TW1611795B, U.S. Pat. No. 7,683,331 B2, CN100374877C, U.S. Pat. No. 6,504,157B2, U.S. Pat. No. 7,968,851 B2, U.S. Pat. No. 7,705,316B2, etc.]most conventional SPECT systems, currently in use or marketed, with one or two heads, either do not allow dynamic tomographic acquisitions, or have a very limited temporal resolution due to detector movement. Because of this, the acquisition of dynamic tomographic imaging and quantification of myocardial blood flow becomes difficult in conventional SPECT systems.

In patent JP4895080B2, a solution is proposed for this problem, in which, for the determination of Cm(t), two static SPECT images of the heart acquired at different times (t1, t2) are used and they obtain Ca(t) from serial extractions of blood from the patient to which corrections are made for concentration of activity of the radiotracer in blood plasma. It should be noted that the collection of blood samples is an invasive and impractical procedure for clinical application. Unlike this background, in the present invention the measurement of Ca(t) and Cm(t) is performed from a single static tomographic image at a given time, which simplifies the procedures of the imaging technique.

In [van den Hoff J., Lougovski A., Schramm G., Maus J., Oehme L., Petr J., Beuthien-Baumann B., Kotzerke J. and Hofheinz F. 2014. Correction of scan time dependence of standard uptake values in oncological PET EJNMMI Res. 4 1-14], the authors demonstrated that the shape of the 18F-FDG radiotracer input function curves (blood tracer concentration) has an invariant shape between patients, as only the scale varies.

In particular, the type of function that best describes the shape of the curve, after the peak activity concentration, is the potential function, in the form according to the following equation:

$$Ca(t) = A.t^{-b} \text{ (for } t > 1 \text{ min, } b > 0) \qquad \text{Equation 4}$$

Where, again, Ca(t) is the arterial concentration of the radiotracer, A is the scale constant, t is the post-injection time of the radiotracer, and b is a constant for each radiotracer. Since b is a constant that defines the shape of the curve, for each particular study the constant A can be cleared by knowing Ca(t) for a known time t. In the present invention it has been verified that the invariance in the shapes of the input curves is also met for myocardial perfusion radiotracer (13N-Ammonia and 99mTc-MIBI). FIGS. 3A and 3B show, for different individuals, the input function curve (Ca(t)), measured in the left ventricle after the peak of maximum activity concentration for 13N-Ammonia.

In patent application CN1 11436959A dynamic PET images of the myocardium are used for the determination of the Ca(t) curve. A static image that is formed from the sum of all frames of the dynamic image is used for image processing (segmenting the heart and obtaining the curves of Ca(t) and Cm(t)). For the determination of the kinetic parameters, compartmental models of several compartments are used. Unlike this background, in the present invention, image acquisition and processing is performed on the basis of a single static tomographic image at a given time (T) and the kinetic parameter K1 is determined using equation 3.

OBJECT OF THE INVENTION

The object of the present invention is a method for quantifying myocardial blood flow that uses a (volumetric/three-dimensional) single static tomographic image of nuclear medicine of the heart and avoids performing standard dynamic tomographic acquisition and the complex procedure associated with it. The method is based on being able to calculate the integral of the activity concentration versus time curve of the blood concentration of the radiotracer from a single temporary sampling point (i.e., time point), as shown in FIG. 4.

The arterial activity concentration Ca(T) of the radiotracer, and the concentration in the myocardium Cm(T) are measured using the static tomographic image, which is acquired only once at a certain time T after administration of the radiotracer, avoiding standard dynamic tomographic acquisition.

DESCRIPTION OF THE DRAWINGS

For clarity and understanding of the object of the present invention, the following figures are presented.

and the coefficient of determination m, for the 34 studies of the exemplary embodiment.

Figure 6:
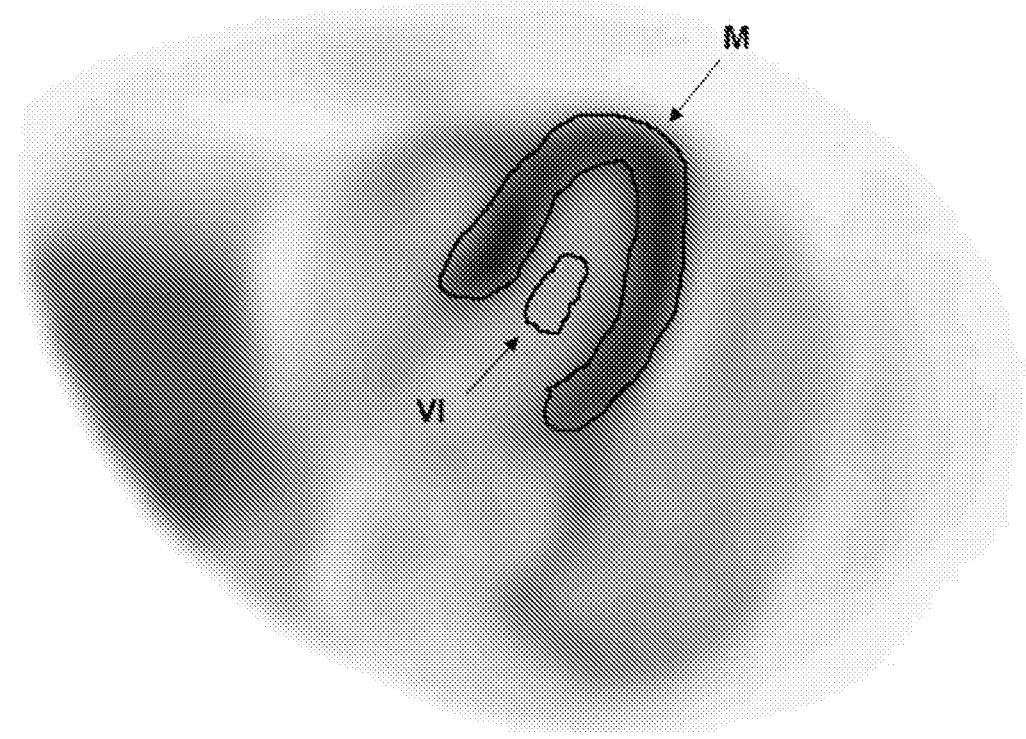

FIG. 6: Segmentation of the left ventricle (LV) and myocardium (M) in static tomographic imaging axial tomography of the heart with PET/CT (Positron Emission Tomography/Multi-Cut Computed Tomography) technique, of the exemplary embodiment.

FIG. 7:
A. Analysis of concordance by Bland-Altman method between the values of K1 obtained in the exemplary embodiment of the method of the present invention (K1) and the validated method (K1c), mentioned in the section of the exemplary embodiment. The solid line shows the mean difference (dm=−0.01) and the dashed lines show the concordance limits (dm±1.96*SD).
B. Analysis of concordance by Bland-Altman method between the values of F obtained by the exemplary embodiment of the method of the present invention (F) and the validated method (Fc), mentioned in the section of the exemplary embodiment. The solid line shows the mean difference (dm=0.12) and the dashed lines show the concordance limits (dm±1.96*SD).

DETAILED DESCRIPTION OF THE INVENTION

Prior to the description of the method proposed in the present invention, a preliminary stage of preparing the individual and a preliminary stage of acquiring and reconstructing a tomographic image are described below, which are not part of the object of the invention, which are required as initial data ("input") for the same:

Preliminary Stage a of Preparing an Individual (not Part of the Object of the Invention):

Following the recommendations of good clinical practices (Argentine Association of Nuclear Biology and Medicine, European Association of Nuclear Medicine, Society of Nuclear Medicine and Molecular Imaging of the United States, among others) for the performance of myocardial perfusion studies with radiotracers, a possible form of preparation of the individual includes the following steps:

1) Determining the conditions under which the myocardial perfusion study will be performed: at rest, during physical exercise, during pharmacological stress or cold test, etc.;
2) Positioning the individual on a PET scanner (or its hybrid variants PET/CT, PET/magnetic resonance imaging (MRI)), SPECT (or its hybrid variants SPECT/CT, SPECT/MRI), or any other nuclear imaging equipment that allows reconstructing images of the activity concentration of a radiotracer, placing the heart in the field of view;
3) Administering a radiotracer for intravenous myocardial perfusion to the individual;
4) Waiting an adequate time before obtaining the static tomographic image to ensure the first transit of the radiotracer through the cardiopulmonary circuit (at least 1 minute after injection);

Preliminary Stage B of Acquiring and Reconstructing Tomographic Image (not Part of the Object of the Invention):

1) Acquiring a volumetric tomographic (3D) image of the heart of the individual, with a duration according to the detection sensitivity of the equipment used and, therefore, to the expected noise level in the reconstructed image, the latter affecting the level of uncertainty in the final calculation (standard deviation/average value);
2) Recording a time T (in seconds) elapsed between the start of the radiotracer injection of step A3) and the start of the acquisition of the static tomographic image of step B1);
3) Reconstructing the image acquired in step B1) using an algorithm that includes a-complete physical model of the imaging process using attenuation correction, scattered radiation correction, dead time, radioactive decay, detector sensitivity and, in the case of PET, random coincidences, and optionally with system spatial resolution and partial volume corrections.

Once the preliminary steps of preparing the individual and acquiring and reconstructing a static tomographic image have been completed, the steps proper to the method object of the present invention are described below:

Stage C of Processing the Tomographic Image

1) Depending on the clinical application, segmenting in the reconstructed image in step B3) the left ventricle, ascending aorta, or other region of interest where the blood activity concentration can be sampled with minimum interference from adjacent tissues, and segmenting the myocardium according to step C2);
2) Depending on the clinical application, maintaining the myocardium as a single region of interest or dividing the myocardium into subregions of interest, which are selected from the group comprising: vascular territories, cardiac segments, and other combinations of voxels. For example, as defined by the American Heart Association, the myocardium is divided into 17 segments [Cerqueira et al, Standardized Myocardial Segmentation and Nomenclature for Tomographic Imaging of the Heart. *Circulation.* 2002|Volume 105, Issue 4: 539-542];
3) Calculating and recording the average of the voxel values of the regions and subregions of interest segmented in said steps C1) and C2), according to the following equation:

$$V_m = \frac{1}{N} \cdot \sum_{i=1}^{N} V_i \qquad \text{Equation 5}$$

wherein:

$V_m$ is the mean value of the N voxel values belonging to the region of interest defined in said steps C1) and C2); and $V_i$ is the value of a single voxel belonging to the region of interest;

Stage D of Calculating the Myocardial Blood Flow

1) Adjust the radiotracer input function (blood activity concentration versus time), using Equation 4: $Ca(t)=A \cdot t^{-b}$ wherein:

Ca(t) is the mean value of the activity concentration, obtained in said step C3) for the left ventricle, for the ascending aorta, or for other region of interest where the blood activity concentration can be sampled with minimum interference from adjacent tissues, representing the concentration of arterial activity at a time t=T, which may or may not be corrected by metabolites;

A is the variable to be adjusted;

T is the post-administration time of the radiotracer in which the acquisition of the static image began, according to step A4) and recorded in step B2);

b is the power coefficient, the value of which is greater than zero. It is a constant that depends on the radiotracer used and the condition of the individual defined in step A1).

In particular, the adjusting action refers to minimizing the distance between the adjusting function and the measured data; for example, by a least squares method (minimization of the L2 norm), or the minimization of the L1 norm.

2) Calculating said coefficient A of said input function, by means of Equation 4 of step D1), by means of the following expression:

$$A = Ca(T) \cdot T^b$$

wherein T is the post-administration time of the radiotracer recorded in said step B2);

3) Calculating the input rate constant of the radiotracer to the myocardium, called K1, measured in [ml/min/$g_{tissue}$] using Equation 3, using the following equation:

$$K1 = m \cdot \frac{Cm(T)}{\int_0^T Ca(t)dt} \qquad \text{Equation 6}$$

wherein:

m is a coefficient that depends on said radiotracer, on said condition of the myocardial perfusion study of said preliminary stage A, and on the population being studied (humans, animals, which could come from different geographical regions, etc.); and Cm(T) is the mean value of the activity concentration, obtained for the myocardium in said step C2) in [Bq/ml];

the integral between the time t=0 and the time t=T of the input function Ca(t), expressed in [Bq*min/ml], is obtained by the following Equation 7a or the following corresponding Equation 7b, according to the value of b:

$$\int_0^T Ca(t) = \frac{A}{1-b} \cdot T^{(1-b)} \; (b \neq 1); \qquad \text{Equation 7a}$$

$$\int_0^T Ca(t) = A \cdot \ln(T) \; (b = 1); \qquad \text{Equation 7b}$$

4) Iteratively calculating the myocardial blood flow, called F, measured in [ml/min/g$_{tissue}$], to a tolerance of at least $1 \times 10^{-3}$ ml/min/g, using the following equation (which results from the combination of Equation 2 and Equation 3):

$$K_1 = F \cdot \left(1 - e^{-\frac{PS}{F}}\right) \qquad \text{Equation 8}$$

being:

$$PS = \alpha + \beta \cdot F \qquad \text{Equation 9}$$

wherein

α and β are coefficients dependent on said myocardial perfusion radiotracer; and the term α+β·F is the surface permeability product of the Renkin-Crone model adapted for multiple capillaries.

For example, the values of α and β for radiotracer 13N-Ammonia and 82Rb are published in [Yoshida K, Mullani N and Gould K L 1996 Coronary flow and flow reserve by PET simplified for clinical applications using rubidium-82 or nitrogen-13-ammonia J. Nucl. Med. 37 1701-12].

Exemplary Embodiment

For the method described in the present invention, the following exemplary embodiment was carried out, which has been contrasted with conventional dynamic studies in order to demonstrate its correct functioning:

34 dynamic resting myocardial flow studies were analyzed, which were performed on individuals with cardiovascular diseases, using PET/CT technique with 13N-Ammonia as a radiotracer. The studies were performed on a GE Healthcare brand PET/CT hybrid scanner, model Discovery 710. The activity administered was 3.2 MBq/kg, using a contrast injector pump with an infusion flow rate of 0.3 ml/s and a total volume of saline solution of 40 ml. The acquisition of the dynamic images began simultaneously with the start of the intravenous injection, using the following sequence of temporal durations: 1 image of 35 seconds, 30 images of 5 seconds each, three images of 20 seconds each, three images of 30 seconds each, and one last image of 5 minutes duration. Each dynamic sequence image was reconstructed with the VuePoint HD iterative algorithm, using 2 iterations, 24 subsets, 2.73 mm voxel size, 3.27 mm slice thickness, and a Gaussian smoothing filter of 7.0 mm full width at half maximum. During the reconstruction, attenuation correction was performed with a computed tomography scan of the same anatomical region, correction of scattered radiation, correction of random coincidences and dead time, correction of sensitivity of the detectors and cross calibration with the dose calibrator.

For each dynamic study, the value of the transfer constant K1c [ml/min/g] and the myocardial flow Fc [ml/min/g] was determined using the software Carimas v2.10, applying the method validated by [DeGrado T R, Hanson M W, Turkington T G, Delong D M, Brezinski D A, Vallée J P, Hedlund L W, Zhang J, Cobb F, Sullivan M J, Coleman R E. Estimation of myocardial blood flow for longitudinal studies with 13N-labeled ammonia and positron emission tomography. J Nucl Cardiol. 1996 November-December; 3(6 Pt 1):494-507. doi: 10.1016/s1071-3581(96)90059-8. PMID: 8989674].

Figure 1:
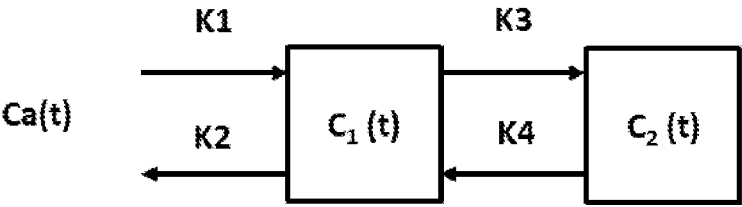
FIG. 1: Example of a two-compartment model and one of the differential equations that describes said model, belonging to the prior art. Ca(t): concentration of arterial activity as a function of time. K1: transfer constant between arterial blood and compartment 1. K2: Transfer constant between compartment 1 and arterial blood. K3: transfer constant between compartment 1 and compartment 2. K4: transfer constant between compartment 2 and compartment 1. C1(t): concentration of activity as a function of time in compartment 1. C2(t): concentration of activity as a function of time in compartment 2.
Figure 2:
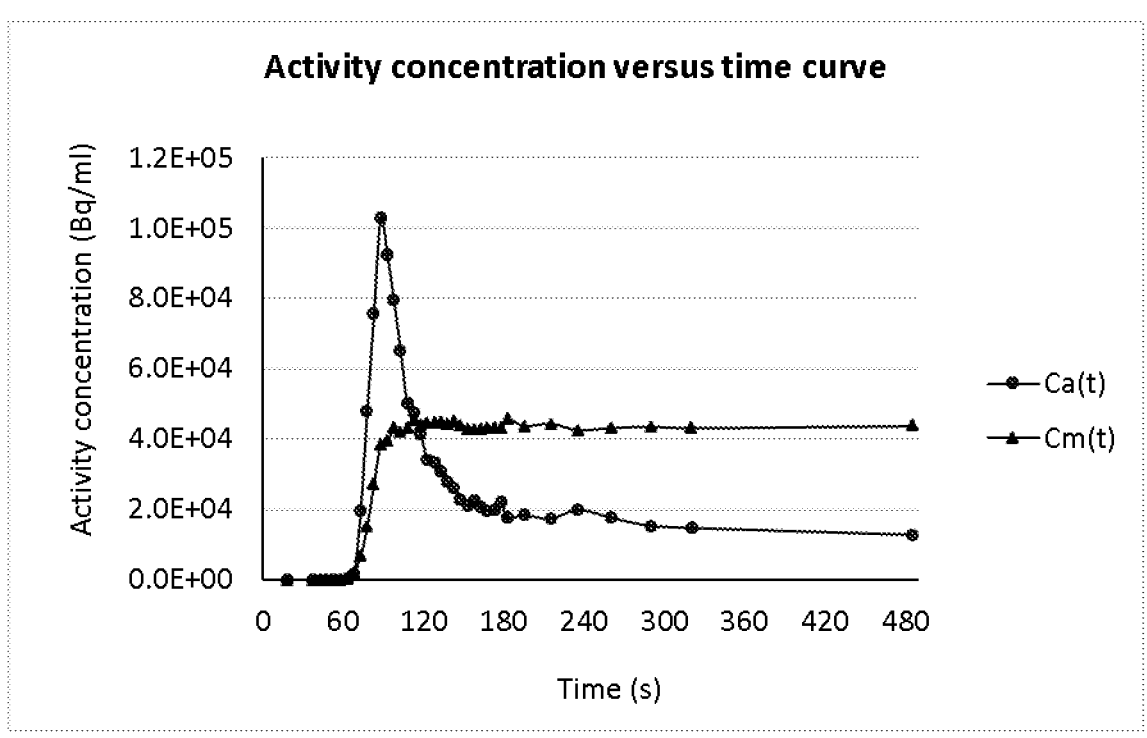
FIG. 2: Activity concentration curve (Bq/ml) of the 13N-Ammonia radiotracer in the left ventricle (Ca(t)) and myocardium (Cm(t)) as a function of time (t), belonging to the prior art.
Figure 3A:
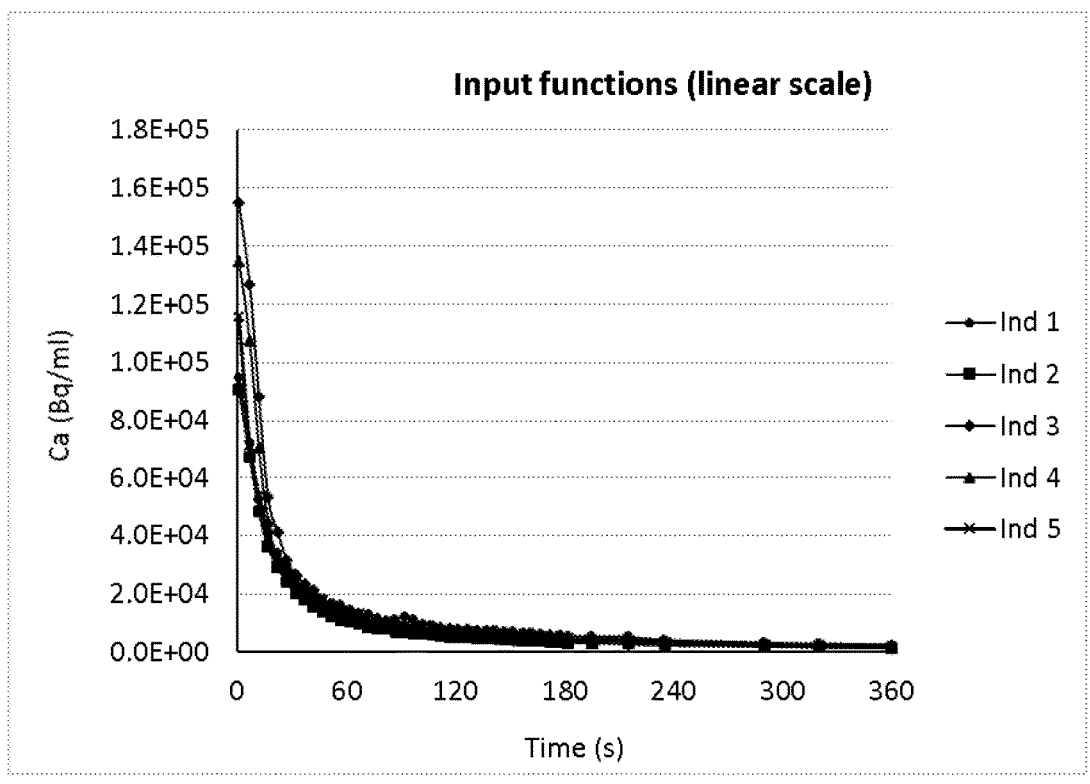
FIG. 3:
A. Input curves of the radiotracer of the exemplary embodiment (13N-Ammonia) in the left ventricle (Ca (t)) after the peak of maximum concentration, for different individuals. Linear scale axes.
B. Input curves of the radiotracer of the exemplary embodiment (13N-Ammonia) in the left ventricle (Ca (t)) after the peak of maximum concentration, for different individuals. Axes in logarithmic scale.
Figure 3B:
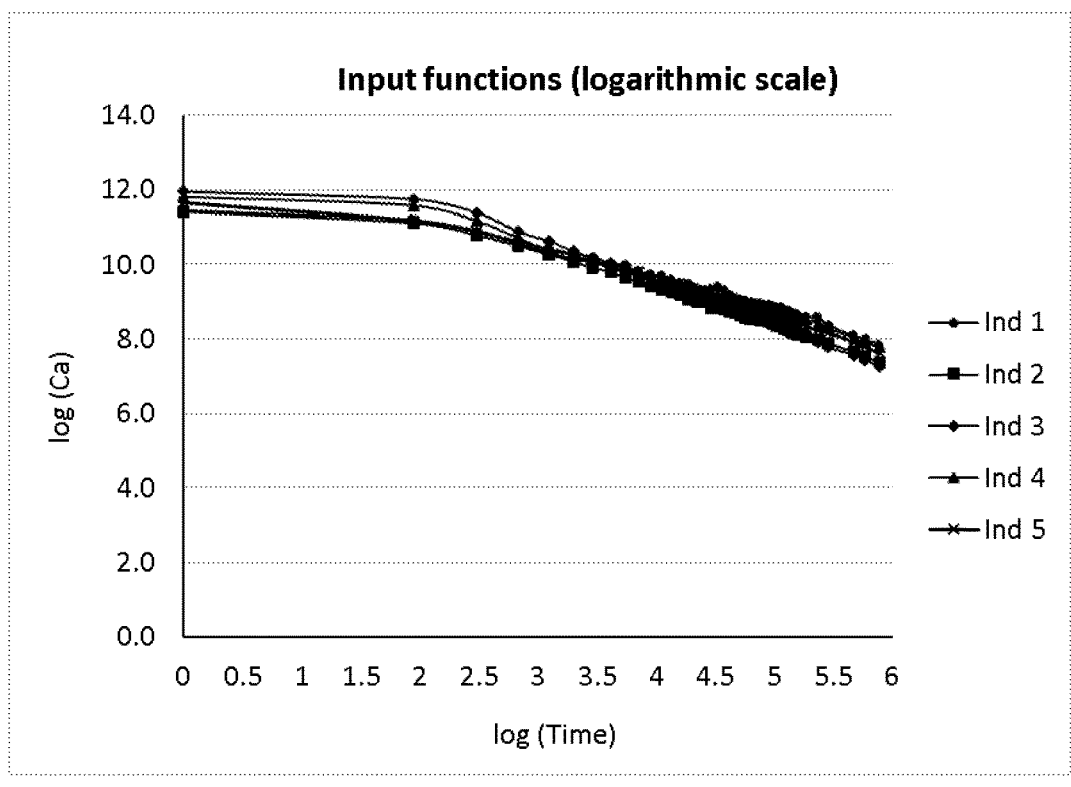
Figure 4:
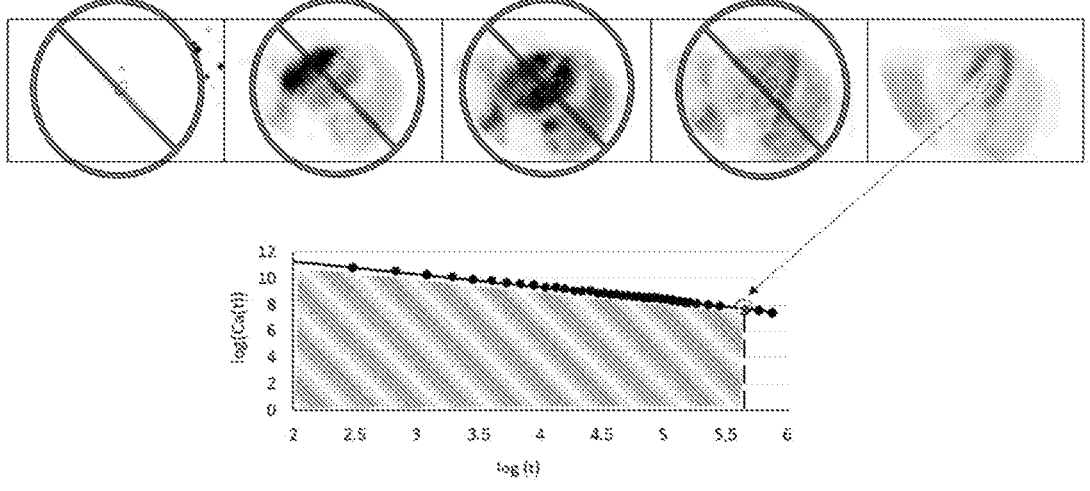
FIG. 4: Graphical representation of the object of the invention. Estimation of the integral of the activity concentration versus time curve of the blood concentration of the radiotracer from a single temporary sampling point (i.e., time point). The line corresponds to the integral between time zero and T(the area under the curve).
Figure 5:
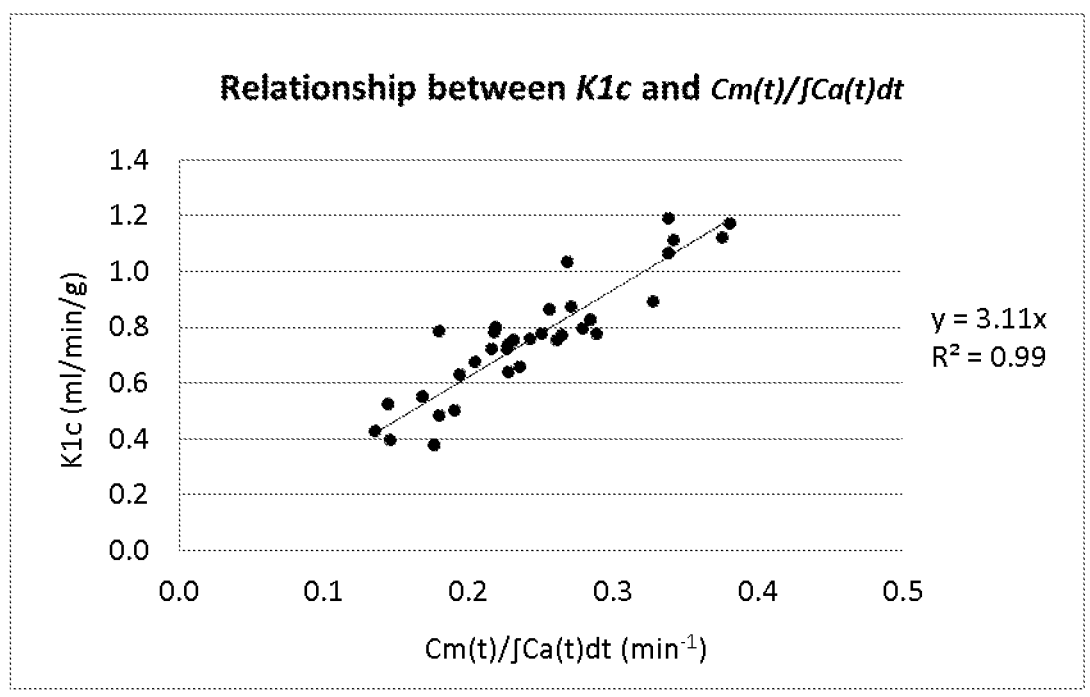
FIG. 5: Graphical representation of the relationship between K1c and $$Cm(T)/\int_0^T Ca(t)dt$$

The value of $$\int_0^t Ca(t)dt$$

up to a time t=T was calculated using the method of the area under the curve, from the curve of Ca(t) measured in the left ventricle of the PET/CT dynamic tomographic image. The relationship between K1c and $$Cm(T)/\int_0^T Ca(t)dt$$

was established using Equation 6 mentioned in step D3) for the studies of the group, determining the coefficient m for the radiotracer used (13N-Ammonia) and the type of study (rest) mentioned above in this example, its value being equal to 3.11 ml/g. Said relationship and the determination of said coefficient m are shown in FIG. 5.

The values of Ca(T) and Cm(T) were obtained by measuring the mean values of voxel in the left ventricle and in the myocardium, respectively, as indicated in steps C1) and C2) of the method of the present invention, employing the static PET/CT tomographic image of the heart, corresponding to a post-administration time T of the radiotracer 13N-Ammonia. FIG. 6 shows the segmentation of the left ventricle (LV) and myocardium (M) in an individual, of the present example.

The arterial entry function Ca(t) was modeled, after the peak of maximum arterial concentration in the left ventricle, by the function described by Equation 4, determining the average power (b=0.4523) for the study group. Ca(t) was used, for t=T, measured in the left ventricle of the PET/CT dynamic tomographic image.

Coefficient A was calculated for each study in the group, using the coefficient b determined above and the Ca(T) values from each study and using the expression mentioned in step D2).

For each study, a new value of $$\int_0^t Ca(t)dt$$

up to a time t=T was calculated using Equation 7a mentioned in step D3) of the method of the present invention, taking into account the coefficients b and A determined in the above paragraphs.

For each study, a new value of the transfer constant K1 was calculated, using Equation 6 mentioned in step D3) of the method of the present invention, using the correlation coefficient m estimated above in the present example and the value of the new relationship $$Cm(T)/\int_0^T Ca(t)dt$$

obtained from the new Ca(t) integral calculated in the previous paragraph.

Figure 7A:
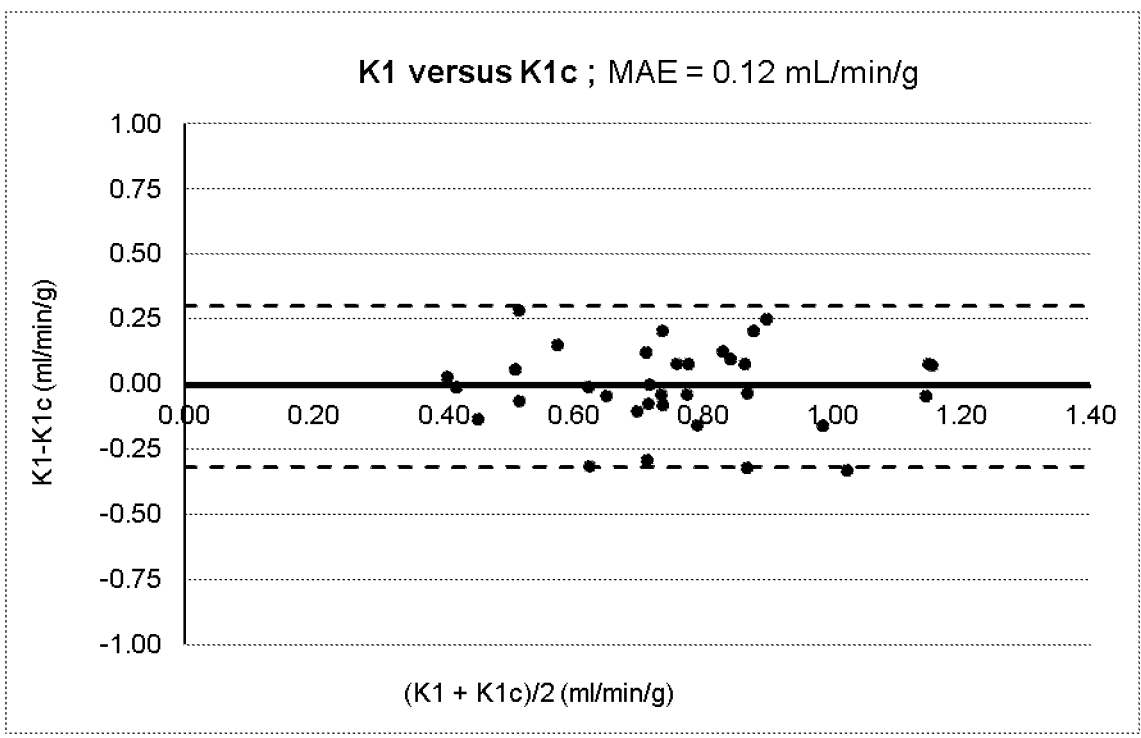

For the transfer constant, the mean absolute error of prediction of the method proposed in the present invention was estimated with respect to the aforementioned validated method, defined as the mean of the absolute differences (or the acronym MAE, mean absolute error) between K1c and K1. FIG. 7A shows the results obtained from the comparison between the two methods.

The time T equal to 360 seconds was obtained by minimizing the MAE and taking into account the best coefficient of determination (FR) corresponding to the determination of said coefficient m.

Figure 7B:
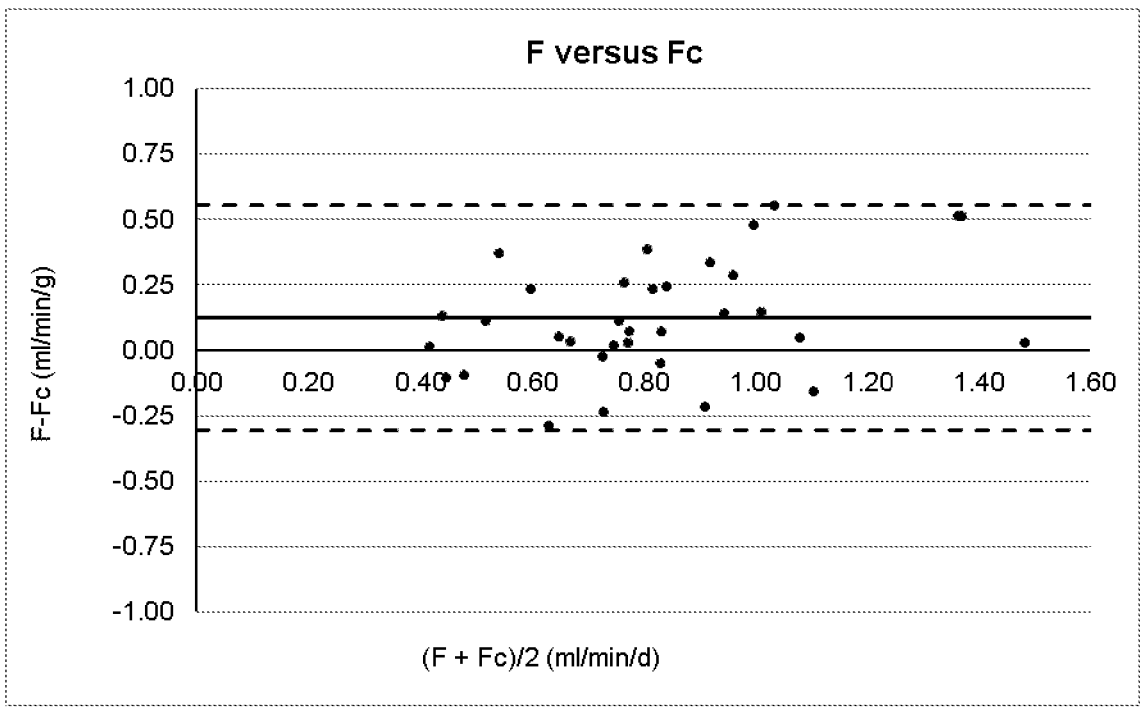

With the K1 values obtained, the value of myocardial blood flow, called F, was determined for each study using Equation 8 and Equation 9, and the coefficients α=1.34 and β=0.48 for 13N-Ammonia, mentioned in step D4) of the method of the present invention. FIG. 7B shows the results obtained from the comparison of the value of F between both methods.

The present invention as defined by a method for quantifying myocardial blood flow from a nuclear medicine tomographic image disclosed in the claims is carried out in a data processing system.

The invention claimed is:

1. A method for quantifying myocardial blood flow from a nuclear medicine tomographic image, comprising:
   a preliminary Stage B of acquiring and reconstructing a tomographic image, comprising the following steps:
      B1) Acquiring a volumetric tomographic image of the heart;
      B2) Recording the time T, in seconds, elapsed between the start of the radiotracer administration of a step A3) of administering a radiotracer to an individual and the start of the acquisition of the static tomographic image of said step B1);
      B3) Reconstructing the image acquired in said step B1);
   wherein said preliminary Stage B is excluded from the present method;
   a Stage C of processing the tomographic image; and
   a Stage D of calculating the myocardial blood flow;

wherein
stage C of processing the tomographic image comprises the following steps:
   C1) depending on the clinical application, segmenting in the reconstructed image in step B3) the left ventricle, ascending aorta or other region of interest where the blood activity concentration can be sampled with minimum interference from adjacent tissues, and segmenting the myocardium according to step C2);
   C2) depending on the clinical application, maintaining the myocardium as a single region of interest or dividing the myocardium into subregions of interest, which are selected from the group comprising: vascular territories, cardiac segments, and other combinations of voxels;
   C3) calculating and recording the average of the voxel values of the regions and subregions of interest segmented in said steps C1) and C2), according to the following equation:

$$V_m = \frac{1}{N} \cdot \sum_{i=1}^{N} V_i$$

wherein:
   $V_m$ is the mean value of the N voxel values belonging to the region of interest defined in said steps C1) and C2);
   $V_i$ is the value of a single voxel belonging to the region of interest;
and wherein said Stage D of calculation comprises the following steps:
   D1) adjusting the input function of said radiotracer (blood activity concentration versus time) using the following equation:

$$Ca(t) = A \cdot t^{-b}$$

wherein:
   Ca(t) is the mean value of activity concentration, obtained in said step C3) for the left ventricle, for the ascending aorta, or for other region of interest where the blood activity concentration can be sampled with minimum interference from adjacent tissues representing the concentration of arterial activity at a time t=T;
   A is the variable to be adjusted;
   T is the post-administration time of the radiotracer recorded in said step B2); and
   b is the power coefficient, whose value is greater than zero, and depends on the radiotracer used and the condition of the study defined in a step A1) of determining the conditions under which the myocardial perfusion study will be performed;
   D2) calculating said coefficient A of said input function, using the equation of said step D1), using the following expression:

$$A = Ca(T) \cdot T^b$$

wherein T is the post-administration time of the radiotracer recorded in said step B2);

D3) calculating the entry constant of the radiotracer to the myocardium, called K1, measured in [ml/min/$g_{tissue}$] using the following equation:

$$K1 = m \cdot \frac{Cm(T)}{\int_0^T Ca(t)dt}$$

wherein:

m is a coefficient that depends on said radiotracer, said condition of the myocardial perfusion study of a preliminary stage A, and the population being studied; and Cm(T) is the mean value of activity concentration, obtained in said step C2) for the myocardium; and D4) iteratively calculating the myocardial blood flow, called F, measured in [ml/min/$g_{tissue}$], until a tolerance of at least $1 \times 10^{-3}$ ml/min/g is achieved, using the following equation:

$$K1 = F \cdot \left(1 - e^{-\frac{\alpha + \beta \cdot F}{F}}\right)$$

wherein $\alpha$ and $\beta$ are coefficients dependent on said myocardial perfusion radiotracer; and the term $\alpha + \beta \cdot F$ is the surface permeability product of the Renkin-Crone model adapted for multiple capillaries.

2. The method for quantifying myocardial blood flow according to claim 1, wherein said region of said step C1) optionally comprises the left ventricle and said regions of said step C2) optionally comprise the complete myocardium.

3. The method for quantifying myocardial blood flow according to claim 1, wherein said region of said step C1) comprises the left ventricle and said regions of said step C2) comprise the three vascular territories.

4. The method for quantifying myocardial blood flow according to claim 1, wherein said region of said step C1) optionally comprises the left ventricle and said regions of said step C2) optionally comprise the 17 cardiac segments.

5. The method for quantifying myocardial blood flow according to claim 1, wherein said region of said step C1) optionally comprises the left ventricle and said regions of said step C2) optionally comprise each voxel of the myocardium.

6. The method for quantifying myocardial blood flow according to claim 1, wherein said region of said step C1) optionally comprises the ascending aorta and said regions of said step C2) optionally comprise the complete myocardium.

7. The method for quantifying myocardial blood flow according to claim 1, wherein said region of said step C1) optionally comprises the ascending aorta and said regions of said step C2) optionally comprise the three vascular territories.

8. The method for quantifying myocardial blood flow according to claim 1, wherein said region of said step C1) optionally comprises the ascending aorta and said regions of said step C2) optionally comprise the 17 cardiac segments.

9. The method for quantifying myocardial blood flow according to claim 1, wherein said region of said step C1) optionally comprises the ascending aorta and said regions of said step C2) optionally comprise each voxel of the myocardium.

10. The method for quantifying myocardial blood flow according to claim 1, wherein said method is carried out in a data processing system.

* * * * *